United States Patent [19]

Muramatsu et al.

[11] Patent Number: 4,517,297

[45] Date of Patent: May 14, 1985

[54] METHOD FOR THE PREPARATION OF PHYSIOLOGICAL EFFECTORS

[75] Inventors: Toshio Muramatsu; Nagao Totani, both of Chiba, Japan; Helmut K. Mangold, Muenster, Fed. Rep. of Germany

[73] Assignee: Röhm GmbH, Darmstadt, Fed. Rep. of Germany

[21] Appl. No.: 605,981

[22] Filed: Apr. 30, 1984

Related U.S. Application Data

[63] Continuation of Ser. No. 400,871, Jul. 22, 1982, abandoned.

[30] Foreign Application Priority Data

Aug. 8, 1981 [DE] Fed. Rep. of Germany ....... 3131524

[51] Int. Cl.$^3$ .......................... C12P 13/00; C07F 9/08
[52] U.S. Cl. .................................................. 435/128
[58] Field of Search ......................... 435/128; 260/925

[56] References Cited

U.S. PATENT DOCUMENTS 4,329,302  5/1982  Hanahan et al. ................... 260/925
4,382,035  5/1983  Eibl ................................. 260/925 X

FOREIGN PATENT DOCUMENTS 1334137 10/1973 United Kingdom .

OTHER PUBLICATIONS

Pugh et al., J. Lipid Research 18, 710–716, (1977).
Demopoulos et al., J. Biol. Chem. 254, 9355–9358, (1979).
Satouchi et al., J. Biol. Chem. 256, 4425–4432, (1981).
Heymans et al., Biochim. Biophys. Acta 666, 230–237, (1981).

Primary Examiner—Lionel M. Shapiro
Attorney, Agent, or Firm—Curtis, Morris & Safford

[57] ABSTRACT

A method for making a biologically active 1-(0-alkyl)- or 1-(0-alkenyl)-2-acetyl-3-phosphorylcholine-sn-glycerol, useful as a pharmaceutical agent or for chemical analysis, from a 1-alkyl- (or 1-alkenyl-)-2,3-diacyl-glycerol.

18 Claims, No Drawings

METHOD FOR THE PREPARATION OF PHYSIOLOGICAL EFFECTORS

This application is a continuation of application Ser. No. 400,871, filed July 22, 1982 now abandoned.

The invention relates to a method for the preparation of compounds suitable for use as physiological effectors and as active substances in pharmaceutical preparations. The compounds prepared by the method of the present invention can also be effectively used in clinical chemical analysis. More particularly, by this invention physiological effectors of the type 1-(0-alkyl)-2-acetyl-3-phosphorylcholine-sn-glycerols are prepared efficiently and with high yield from 1-(0-alkyl)-2,3-diacyl-glycerols, 1-(0-alkenyl)-2,3-diacyl-glycerols or 1-(0-alkenyl)-2-acetyl-3-phosphorylcholine-sn-glycerols.

The complex process of blood clotting is controlled by the interaction of a whole series of so-called "factors". The factor in the blood which is responsible for the aggregation of blood platelets, the Platelet Activating Factor (PAF), has proved to be very difficult to identify.

Not until recently has it been possible to demonstrate that certain compounds of formula I, $$\begin{array}{c} \quad O \quad\quad H_2C-OR \\ \quad \| \quad\quad | \\ CH_3-C-O-CH \quad O^\ominus \\ \quad\quad\quad | \quad\quad | \\ \quad H_2C-O-P-O(CH_2)_2-\overset{\oplus}{N}-(CH_3)_x \\ \quad\quad\quad \| \quad\quad\quad | \\ \quad\quad\quad O \quad\quad\quad (H)_y \end{array} \quad (I)$$

wherein X stands for an integer from 1 to 3, and y is 0, 1 or 2 and the sum of x plus y is always 3, with I: R=alkyl or alkenyl
IAa: R=$C_{16}H_{33}$ x=3
IAb: R=$C_{18}H_{37}$ x=3, namely, the compounds of formulas IAa and IAb (in combination, formula IA), possess the activity of the Platelet Activating Factor. (See Demopoulos et al J. Biol. Chem. 254, 9355 (1979); Godfroid et al, FEBS Letters Vol. 116 No. 2, pages 161-164 (1980); Blank et al, Biochemical and Biophysical Research Communications Vol. 90, No. 4, pages 1194-1200 (1979)).

In the light of what is known at present, the compounds of formulas IAa and IAb may be combined into a unit (PAF). Apart from the substituent R, where some variability is permissible, a strict correlation appears to exist between structure and biological effect. (Chem. & Eng. News, Apr. 13, 1981, 28.)

In addition to blood-platelet aggregation and secretion, the compounds of formula IA produce further biological reactions in warm-blooded animals. For example, in humans they exhibit vascular activity. In experiments with animals, they were found to lower the blood pressure significantly. Investigation of the Platelet Activity Factor has always been very difficult because of the difficulty of identifying this factor.

A method of preparing specific compounds representative of formula I has been described in J. Biol. Chem. 256, 4425 (1981). Mixtures of such compounds have been prepared by C. A. Demopoulos et al. from the choline plasmalogens of bovine hearts (J. Biol. Chem. 254, 9355 (1979).)

However, the known methods have failed to satisfy the requirements of practical synthesis in that they are too time-consuming and the yields achieved are quite unsatisfactory.

Thus a need exists for a method of preparation of compounds of formula I exhibiting greater ease of preparation by synthetic or semi-synthetic means. This need is satisfied by the method of the present invention described herein. It is accordingly an object of the present invention to provide a novel method for the synthesis of compounds represented by formula I which method exhibits a level of process efficiency and ease of control heretofore unknown and unexpected. Furthermore, the compounds synthesized in accordance with applicants' invention can be effectively used as physiological effectors, in pharmaceutical preparations and in clinical chemical analysis.

It has now been found that compounds of formula I can be readily prepared from 1-alkyl-2,3-diacyl-glycerols of formula II, $$\begin{array}{c} H_2C-OR' \\ | \\ Ac-O-CH \\ | \\ H_2C-O-Ac \end{array} \quad (II)$$

wherein R' stands for an alkyl radical $R_1$, preferably of the formula $(CH_2)_n-CH_3$ wherein n stands for an odd number between 13 and 23, or an unsaturated alkyl radical $R_2$ with the same number of carbon atoms, preferably of the formula $-(CH_2)_m-CH=CH-(CH_2)_p CH_3$, wherein m and p are integers and the sum of m and p is between 11 and 21, and particularly, wherein $R_2$ represents a $-(CH_2)_8-CH=CH-(CH_2)_7-CH_3$ group and Ac is an acyl radical, optionally an unsaturated acyl radical, and preferably a palmitoyl and/or oleoyl radical.

Particularly preferred is a synthesis based on the 1-alkyl-2,3-diacylglycerols of formula IIA, $$\begin{array}{c} H_2C-OR' \\ | \\ Ac-O-CH \\ | \\ H_2C-O-Ac \end{array} \quad (IIA)$$

wherein IIA
  a R'=$C_{16}H_{33}$
  b R'=$C_{18}H_{37}$
  c R'=$(CH_2)_6-CH=CH-(CH_2)_7-CH_3$ or a $C_{16}H_{31}$ isomer
  d R'=$(CH_2)_8-CH=CH-(CH_2)_7-CH_3$ or a $C_{18}H_{35}$ isomer and wherein Ac has the meaning given above.

A particularly interesting aspect of the method in accordance with the invention is based on the observation that the starting material of formula IIA can be obtained in adequate quality and sufficient quantity from natural sources. Particularly suitable for use as the starting material for formulas IIA and IIBb is fish liver oil including oil from the liver of the Pacific ratfish (*Hydrolagus colliei* or *Hydrolagus novozealandiae*), the spiny dogfish (*Squalus acanthias*), the Atlantic chimaera (*Chimaera monstrosa*) or the Greenland shark (*Sommiosus Microcephalus*), or any combination thereof. The composition of the liver oil from *Hydrolagus colliei* and *Chimaera monstrosa* typically is about 25 weight percent triacylglycerols, 66 weight percent 1-alkyl-2,3-diacylglycerols, essentially of formula IIA, and about 6 weight percent 1-(1′alkenyl)-2,3-diacylglycerols. The extraction of these oils is known per se.

As a basis, about 17% of the hexadecyl ether and about 78% of the octadecyl ether may be assumed to be present. For purposes of description of the present invention, the liver oil from *Hydrolagus colliei* and *Chimaera monstrosa* will hereinafter be referred to as "liver oil". The liver oil from the spiny dogfish (*Squalus acanthias*) can be used in the same way.

In a first reaction step, the liver oil is subjected to enzymatic hydrolysis, which yields compounds of the formula IIIA,

(IIIA)

wherein $R'_1$ has the same meaning as $R'$ in formula IIA (IIIa $R'_1=C_{16}H_{33}$, IIIb $R'_1=C_{18}H_{37}$, IIIc $R'_1=C_{16}H_{31}$, IIId $R'_1=C_{18}H_{35}$) and Ac has the meaning given above, as well as 2-acylglycerols and fatty acids.

When unsaturated compounds are involved, it is advantageous to operate under an inert protective gas such as, for example, pure nitrogen. Dissolved oxygen is preferably removed from the water used.

The enzymatic hydrolysis may be carried out with suitable lipolytic enzymes (characterized by the E. C. number 3.1.1.3), and in particular pancreatic lipase (steapsin). It may be performed in the manner described by F. E. Luddy et al., J. Am. Oil Chem. Soc. 41, 693 (1964). It is advantageous to use an emulsion of the liver oil in a buffer solution suited for the enzymatic reaction as, for example, in a buffer solution with a pH of 7.0 to 8.5 and preferably a pH of 8.

The buffer may be a tris buffer, for example. Suitable emulsifiers are enzyme-compatible emulsifiers of the oil-in-water (o/w) type such as the emulsifying components of bile (salts of bile acids).

The enzymatic reaction may be carried out at temperatures ranging from room temperature to elevated temperature depending upon the activity characteristics of the enzyme or enzymes used.

Separation from the primarily hydrophilic products of the first reaction step can then be advantageously effectuated by extraction with a suitable extractant, preferably one that can also be used in the further treatment. For example, an ether such as diethyl ether or diisopropyl ether is suitable.

After appropriate preparation (e.g., drying and volume reduction), hydrogenation may, if necessary, be carried out in a second reaction step in known manner to convert the unsaturated compounds of formulas IIIc and IIId into saturated compounds such as IIIa and IIIb and compounds of formula IIIA. Hydrogenation can be carried out with hydrogen using conventional catalysts. For example, metal catalysts can be used advantageously by making use of technical know-how gained in the hardening of fats. For the preparation of $H^3$-tagged compounds, tritium may be used in place of hydrogen in a manner known in the art.

As an example of a catalyst, platinum in the form of platinic oxide may be used. Hydrogenation is usually carried out at slightly elevated pressure.

Following appropriate further treatment (e.g. distilling off the solvent and drying the residue by azeotropic distillation of water with dry benzene, pyridine, etc.), the product of the second reaction step is phosphorylated by reaction with the compound of formula IV,

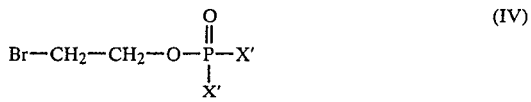
(IV)

wherein X′ stands for chlorine or bromine, preferably in a suitable solvent such as, for example, a halogenated hydrocarbon such as trichloroethylene or chloroform, an ether such as dioxane, tetrahydrofuran, or an aromatic hydrocarbon such as toluene, preferably in the presence of a proton acceptor such as a tertiary amine, with stirring and optionally with addition of heat under an inert dry protective gas such as nitrogen. Then, preferably without isolation of the product formed, (1-alkyl-2-acylglycero-3-)(β-bromoethyl)phosphoric acid halide, and after separation of the precipitate formed and elimination of the solvent by evaporation in vacuum, treatment with an aqueous solution is carried out, preferably by dissolution in a water-miscible, inert solvent such as tetrahydrofuran or dioxane in a buffer solution and in the presence of EDTA, for example, preferably in the alkaline range at a pH of 10 for example, and in a controlled manner and within a relatively short time such as for half an hour. Extraction is then carried out with a suitable extractant such as diisopropyl ether, for example, and after the latter has been eliminated by evaporation in vacuum for example, a third reaction step is carried out in a suitable solvent such as a mixture of a halogenated hydrocarbon such as chloroform, a nitrile such as acetonitrile, and an alcohol such as isopropanol, with an amine of formula V,

wherein x and y have the meanings given above, preferably with the addition of heat, at a temperature of 50° C., for example, and over a period of several hours, for example, about 5 hours, to give the compound of formula VI,

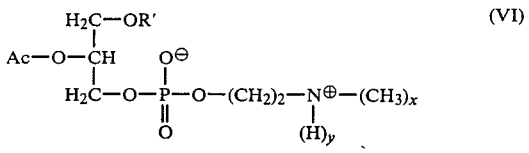
(VI)

Traces of trimethylamine may then be eliminated, for example, with chloroform/methane (i.e., 2:1 by volume) and chloroform.

As a fourth reaction step, the acyl group is hydrolyzed off in the 2 position, for example, by reacting the compound of formula VI, dissolved in a suitable solvent such as a halogenated hydrocarbon, with alcoholates for example, 0.33N methanolic KOH, at room temperature.

The hydrolyzate is neutralized, for example, by the addition of ethyl formate with stirring. Then an extractant such as chloroform is added, followed by methanol and water. After repeated extractions, the extractant is eliminated by evaporation in vacuum for example, and the residue is dried, for example, by treatment with a solvent forming an azeotrope. (Chloroform/methanol [2:1 by volume], followed by chloroform.)

The product may then be dissolved once more in chloroform and the substance precipitated with acetone at reduced temperature for example. The fourth reaction step yields compounds of the type of 1-alkyl-glycero-3-phosphocholine represented by compounds of formula VII,

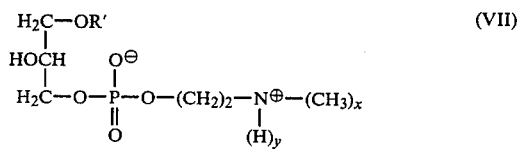

wherein R', x and y have the meanings given above. In the final and fifth reaction step, an acetyl group is introduced conventionally into the compound of formula VII in the 2 position, the desired compounds of formula IA being thus obtained by acetylation with acetic anhydride in a suitable solvent such as an aromatic solvent like benzene or toluene, a nitrile such as acetonitrile, or a mixture of solvents and preferably with heating to about 80° C. for example for about 4 to 5 hours, and with the addition of catalysts such as pyridine compounds like dialkylaminopyridines. The further working up can be performed in the usual way.

After elimination of the volatile constituents in a rotary evaporator at about 40° C., purification to give compounds of formula IA can be carried out by conventional chromatographic methods. The compounds obtained in the fifth reaction step have the formula IA. With respect to their properties, so far as can be determined, they have been found to be identical with the Platelet Activating Factor (PAF). The yields based on the starting product of formula IIA are quite satisfactory. By this invention a novel method which is attractive from the standpoint of simplicity and economy in the production of the class of compounds (I) to which said effectors of formula IA belong is provided to the industry. Furthermore, a technically interesting method for preparation of the compounds of formula VII which likewise exhibit biological activity, is provided herein.

The examples which follow are provided as an illustration of the method of the invention.

ANALYSIS

The analysis of the starting, intermediate and end compounds may be performed by thin-layer chromatography on Silica Gel 60 (DC aluminum foil, manufactured by E. Merck AG) in an n-hexane/diethyl ether/acetic acid solvent system (60:40:1 by volume) in the case of neutral compounds, and in a chloroform/methanol/acetic acid/water system (50:25:8:4 by volume) in the case of ionic lipids.

Preparative separations may be effected on Silica Gel H (0.5 mm layer) of E. Merck AG in the last-mentioned system and in a methanol/water system (2:1 by volume). To render the substance visible, the molybdenum-blue reagent used by J. C. Dittmer & R. L. Lester (J. Lipid Res. 5, 126 [1964]) or blackening by heating with concentrated sulfuric acid may be utilized.

The gas-chromatographic determination was made at 220° C. with a Perkin-Elmer F22 GAS Chromatograph (Perkin-Elmer & Co. GmbH, Bodenseewerk) using a 200×0.5 cm gas column containing 10% Silar on Gas Chrome Q (Applied Science Laboratories, Inc., State College, Pa. 16801).

SYNTHESIS

To the extent that unsaturated lipids were involved, a pure-nitrogen atmosphere was used to the extent possible.

The oxygen was removed from the water used by boiling and cooling under nitrogen.

Unless otherwise noted, the percentages indicated are weight percent.

FIRST REACTION STEP (ENZYMATIC HYDROLYSIS; FORMULAS IIA AND III)

2.0 g liver oil from *Hydrolagus colliei* (corresponding to 1.6 millimoles of compound IIA) was emulsified in a 100-ml centrifuge tube with 40 ml tris-HCl buffer of pH 8, 5 ml of an aqueous 22% calcium chloride solution and 10 ml of an 0.1% solution of salts of bile acids. The ester linkage in the 1 (or 3) position of the glycerolipids was hydrolytically split by the addition of 900 mg pancreatin with occasional agitation at 40° C. over a period of 1.5 hours. The emulsion so obtained was cooled to room temperature and extracted with three 30 ml portions of diisopropyl ether, the phases then being separated by centrifugation.

SECOND REACTION STEP (HYDROGENATION; FORMULAS IIIc AND IIId, IIIa AND IIIb)

The diisopropyl ether phase was dried over anhydrous sodium sulfate, concentrated in a rotary evaporator to about one-half, and hydrogenated for 3 hours over 200 mg platinic oxide at a pressure of 50 psi. The catalyst was removed by centrifugation and washing was effected with 20 ml diisopropyl ether. The ether fractions were combined and the ether was eliminated in a rotary evaporator. Traces of water in the somewhat yellowish residue were eliminated by two distillations with 30 ml benzene each.

The reaction can be carried out similarly with tritium in place of hydrogen.

The crude product of formula III could be used "as is" in the next reaction step.

THIRD REACTION STEP (PHOSPHORYLATION AND REACTION WITH TRIMETHYLAMINE; FORMULA III→FORMULA VI)

1.3 g 2-bromoethylphosphoric dichloride was dissolved in 20 ml trichloroethylene in a three-neck flask and cooled in an ice-water bath. After the addition of a mixture of 30 ml trichloroethylene and 1.5 triethylamine, the solution was heated to 30° C. and a stream of dried nitrogen was passed through for 10 minutes. To this solution was added the product of the preceding second reaction step (compound of formula III) in 30 ml trichloroethylene, and 1.5 ml triethylamine was added through a dropper funnel at 30° C. over a period of 1.5 hours with vigorous stirring. Stirring was continued for another 30 minutes, and the precipitate formed was removed by filtration and the filtrate concentrated by evaporation.

The reddish, oily residue was dissolved in 10 ml tetrahydrofuran. Solutions of 10 ml aqueous 0.5M sodium acetate and 0.7 ml aqueous 0.5M ethylenediamine tetraacetic acid (pH 10.5) were added and the mixture was stirred for 30 minutes. The reaction mixture was diluted with 15 ml water and then extracted with two 100-ml portions of diisopropyl ether. After evaporation of the solvent, the oily residue was dissolved in a mixture of 8 ml chloroform, 13 ml isopropanol and 13 ml acetonitrile. To this solution there was added 16 ml aqueous triethylamine (45%) at 50° C. with stirring and the reaction was continued for 5 hours. The orange-colored solution was concentrated in a rotary evaporator, and traces of triethylamine were eliminated by distillation with chloroform/methanol (2:1 by volume) and chloroform. The residue could be used "as is" in the next reaction step.

FOURTH REACTION STEP (HYDROLYSIS OF THE ACYL RADICAL→FORMULA VII)

The crude product of the preceding reaction step, of formula VI, was dissolved in 100 ml chloroform and treated for one hour at room temperature with 50 ml 0.33N methanolic KOH. The hydrolyzate was neutralized by the addition of 15 ml ethyl formate and stirred for 15 minutes at room temperature. Then 30 ml chloroform, 45 ml methanol and 60 ml water were added. The chloroform phase was withdrawn, and the aqueous-alcoholic phase was extracted with two portions of 30 ml chloroform each. The chloroform phases were combined, the chloroform was eliminated in a rotary evaporator, and traces of water were removed by repeated distillation with chloroform-methanol (2:1 by volume) and chloroform.

A solution of the residue in 20 ml chloroform was charged to a 100-ml centrifuge beaker, mixed with a total of 70 ml acetone in small portions, and stored overnight at 5° C. The yellowish precipitate formed was separated by precipitation through centrifugation at −10° C. and then dissolved in 10 ml chloroform. The solution so obtained was mixed with a total of 50 ml acetone in small portions and stored for 3 hours at 5° C.

The precipitate formed was separated by centrifugation and dried in a vacuum desiccator for several hours over calcium chloride. The somewhat yellowish, hygroscopic product could be used directly in the next reaction step.

FIFTH REACTION STEP (ACETYLATION OF FORMULA VII→FORMULA IA)

The dry product from the fourth reaction step (formula VII, 1 millimole) was suspended in a mixture of 7 ml benzene and 5 ml acetonitrile to which 0.4 ml (about 4 millimoles) acetic anhydride had been added. The mixture was heated to between 60° and 80° C. After cooling to room temperature, 150 mg 4-dimethylaminopyridine was added. The suspension was held at room temperature for 4 to 5 hours. The solvent was eliminated in a rotary evaporator at 40° C., the yellowish residue was dissolved with some chloroform, and separation was effected on Silica Gel H layers. The fraction containing the end product of formula IA was scraped off and the desired product eluted with methanol.

After the solvent had been distilled off in a rotary evaporator, 10 ml acetone was added to the colorless residue. The solution was held at −10° C. for a few hours with occasional stirring. Centrifugation yielded the colorless residue, which was dried in a vacuum desiccator over calcium chloride. The compound of formula IA was obtained in an amount of 0.35 g (10.65 millimoles, corresponding to a total yield of 24%). Melting point: 220° C. (decomp.) $[\alpha]^{23}_D = 3.0$ (c = 0.6 in CHCl$_3$). IR absorption = 1060, 1100, 1120 cm$^{-1}$ (P—O—C C—O vibrations) 1240 cm$^{-1}$ (P=O, 1740 cm$^{-1}$ (C=O) 2850, 2920 cm$^{-1}$ (C—H).

PREPARATION OF THE COMPOUNDS OF FORMULA IV

The compounds of formula IV, such as bromoethylphosphoric dichloride, can be prepared conventionally, for example, by reacting 2-bromoethanol with phosphorus oxychloride. (See H. Eibl & A. Nicksch. Chem. Phys. Lipids 22, 1 [1978].)

We claim:

1. A method for making a compound of the formula

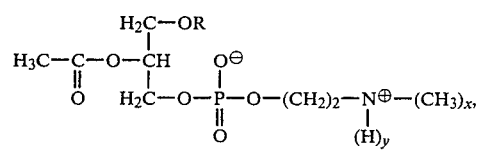

wherein R is alkyl or alkenyl, x is 1, 2, or 3, y is 0, 1, or 2, and (x+y) is 3, which method comprises partially deacylating a starting compound of the formula

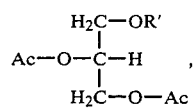

wherein R' is alkyl or alkenyl and Ac is fatty acid acyl, to form a first intermediate of the formula

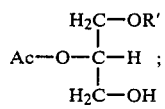

reacting said first intermediate with a bromoethylphosphoric acid halide of the formula

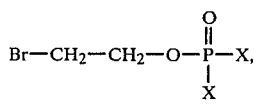

wherein X is bromine or chlorine, to form a second intermediate;

reacting said second intermediate with an amine of the formula

to form a third intermediate of the formula

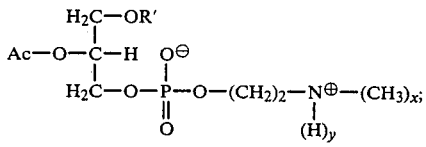

hydrolyzing said third intermediate to form a fourth intermediate of the formula

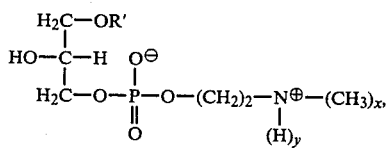

and then acetylating said fourth intermediate to form the desired compound.

2. A method as in claim 1 wherein R and R' are each alkyl of the formula $C_{16}H_{33}-$ or $C_{18}H_{37}-$.

3. A method as in claim 2 wherein said alkyl is linear alkyl.

4. A method as in claim 1 wherein R and R' are each alkenyl of the formula $C_{16}H_{31}-$ or $C_{18}H_{35}-$.

5. A method as in claim 4 wherein said alkenyl is linear alkenyl.

6. A method as in claim 1 wherein said starting compound is derived from fish liver oil.

7. A method as in claim 6 wherein said fish liver oil is an oil extracted from a fish selected from the group consisting of *Hydrolagus colliei, Hydrolagus novozealandiae, Squalus acanthias, Chimaera monstrosa,* and *Sommiosus microcephalus,* or is a combination of such oils.

8. A method as in claim 7 wherein R and R' are each alkenyl, and said first intermediate is catalytically hydrogenated so that R' is alkyl.

9. A method for making a compound of the formula

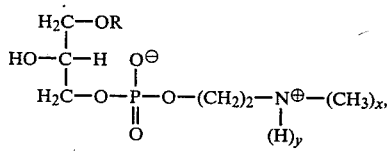

wherein R is alkyl or alkenyl, x is 1, 2, or 3, y is 0, 1, or 2, and (x+y) is 3, which method comprises
partially deacylating, with a lipolytic enzyme, a starting compound of the formula

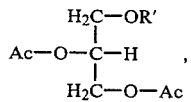

wherein R' is alkyl or alkenyl and Ac is fatty acid acyl, to form a first intermediate of the formula

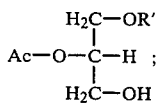

reacting said first intermediate with a bromoethylphosphoric acid halide of the formula

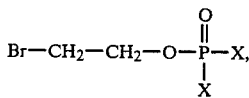

wherein X is bromine or chlorine, to form a second intermediate;
reacting said second intermediate with an amine of the formula $(H)_y N(CH_3)_x$ to form a third intermediate of the formula

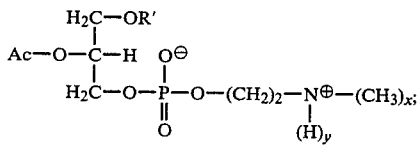

and hydrolyzing said third intermediate to form the desired compound.

10. A method as in claim 9 wherein said desired compound is subsequently acetylated to form a compound of the formula

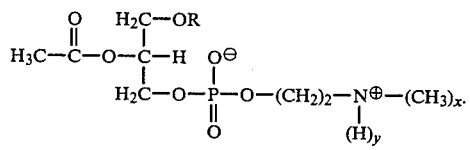

11. A method as in claim 9 wherein R and R' are each alkyl of the formula $C_{16}H_{33}-$ or $C_{18}H_{37}-$.

12. A method as in claim 11 wherein said alkyl is linear alkyl.

13. A method as in claim 10 wherein R and R' are each alkenyl of the formula $C_{16}H_{31}-$ or $C_{18}H_{35}-$.

14. A method as in claim 13 wherein said alkenyl is linear alkenyl.

15. A method as in claim 9 wherein said starting compound is derived from fish liver oil.

16. A method as in claim 15 wherein said fish liver oil is an oil extracted from a fish selected from the group consisting of *Hydrolagus colliei, Hydrolagus novozealandiae, Squalus acanthias, Chimaera monstrosa,* and *Sommiosus microcephalus,* or is a combination of such oils.

17. A method as in claim 9 wherein R and R' are each alkenyl, and said first intermediate is catalytically hydrogenated so that R' is alkyl.

18. A method as in claim 10 wherein R and R' are each alkenyl, and said first intermediate is catalytically hydrogenated so that R' is alkyl.

* * * * *